(12) United States Patent
Yang et al.

(10) Patent No.: US 11,020,194 B2
(45) Date of Patent: Jun. 1, 2021

(54) MINIMALLY INVASIVE SURGICAL INSTRUMENTS WITH TERMINAL STEERABLE MECHANISM

(71) Applicant: NATIONAL CHIAO TUNG UNIVERSITY, Hsinchu (TW)

(72) Inventors: Bing-Shiang Yang, Hsinchu (TW); Chao-Che Wu, New Taipei (TW)

(73) Assignee: NATIONAL CHIAO TUNG UNIVERSITY, Hsinchu (TW)

(*) Notice: Subject to any disclaimer, the term of this patent is extended or adjusted under 35 U.S.C. 154(b) by 100 days.

(21) Appl. No.: 15/980,130

(22) Filed: May 15, 2018

(65) Prior Publication Data
US 2019/0125469 A1    May 2, 2019

(30) Foreign Application Priority Data

Nov. 2, 2017  (TW) .................................. 106137978

(51) Int. Cl.
*A61B 34/00* (2016.01)
*A61M 1/00* (2006.01)
(Continued)

(52) U.S. Cl.
CPC .......... *A61B 34/71* (2016.02); *A61B 1/00039* (2013.01); *A61B 1/0052* (2013.01);
(Continued)

(58) Field of Classification Search
CPC .......... A61M 25/0147; A61M 25/0133; A61B 2017/00238; A61B 2017/003;
(Continued)

(56) References Cited

U.S. PATENT DOCUMENTS 3,958,566 A   5/1976   Furihata
5,322,506 A   6/1994   Kullas
(Continued)

FOREIGN PATENT DOCUMENTS

CN    2852465 Y    12/2006
CN    201806687 U   4/2011
(Continued)

OTHER PUBLICATIONS

Ho et al., "Towards a MRI-Compatible Meso-Scale SMA-Actuated Robot using PWN Control," ResearchGate, Oct. 2010, 8 pages.
(Continued)

*Primary Examiner* — Nathan R Price
*Assistant Examiner* — Tania Ismail
(74) *Attorney, Agent, or Firm* — Birch, Stewart, Kolasch & Birch, LLP

(57) ABSTRACT

The present invention provides a minimally invasive surgical instrument with a terminal steerable mechanism, comprising an intervention device, a control device and one or more wires. The strip-shaped intervention device sequentially includes a main section, a flexible section and an operation section from the top to the end. The control device includes a sphere with a preset rotational degree of freedom, and an operating lever connected to the sphere. Said one or more wires are extended along the main section of the intervention device. Here, the second ends of said at least one or more wires are connected to the flexible section or the operation section of the intervention device, and the first ends thereof are connected to at least a part of the control device.

19 Claims, 14 Drawing Sheets

(51) Int. Cl.
    *A61M 5/14* (2006.01)
    *A61M 25/01* (2006.01)
    *A61B 1/005* (2006.01)
    *A61B 1/00* (2006.01)
    *A61B 18/12* (2006.01)
    *A61B 34/37* (2016.01)
    *G05G 9/047* (2006.01)
    *A61B 17/00* (2006.01)
    *A61B 34/30* (2016.01)
    *G05G 9/053* (2006.01)

(52) U.S. Cl.
    CPC ........... *A61B 1/0057* (2013.01); *A61M 1/008* (2013.01); *A61M 5/14* (2013.01); *A61M 25/0113* (2013.01); *A61B 1/00142* (2013.01); *A61B 18/12* (2013.01); *A61B 34/37* (2016.02); *A61B 2017/003* (2013.01); *A61B 2017/00238* (2013.01); *A61B 2017/00318* (2013.01); *A61B 2034/303* (2016.02); *A61B 2034/305* (2016.02); *A61B 2034/742* (2016.02); *A61B 2560/0406* (2013.01); *A61M 25/0136* (2013.01); *A61M 2205/05* (2013.01); *A61M 2210/0693* (2013.01); *G05G 9/047* (2013.01); *G05G 9/053* (2013.01); *G05G 2009/04707* (2013.01); *G05G 2009/04711* (2013.01)

(58) Field of Classification Search
    CPC .......... A61B 2017/00318; A61B 34/71; A61B 1/0052; A61B 1/0057; A61B 2034/742; G05G 9/047; G05G 9/053; G05G 2009/04707; G05G 2009/04711
    See application file for complete search history.

(56) References Cited

U.S. PATENT DOCUMENTS

| | | | |
|---|---|---|---|
| 5,429,596 A | 7/1995 | Arias et al. | |
| 5,484,402 A | 1/1996 | Saravia et al. | |
| 8,403,831 B2 | 3/2013 | Kishioka | |
| 8,409,245 B2* | 4/2013 | Lee | A61B 17/00234 606/205 |
| 9,907,457 B2 | 3/2018 | Grant et al. | |
| 2001/0002127 A1* | 5/2001 | Cheng | G05G 9/047 345/161 |
| 2008/0236575 A1 | 10/2008 | Chuda | |
| 2011/0004225 A1 | 1/2011 | Choi et al. | |
| 2012/0226149 A1* | 9/2012 | Greenburg | A61B 1/0125 600/424 |
| 2013/0102846 A1* | 4/2013 | Sjostrom | A61B 1/008 600/110 |

FOREIGN PATENT DOCUMENTS

| | | | | |
|---|---|---|---|---|
| CN | 201987528 U | 9/2011 | | |
| CN | 102256550 A | 11/2011 | | |
| CN | 204332792 U | 5/2015 | | |
| CN | 204500754 U | 7/2015 | | |
| CN | 204581209 U | 8/2015 | | |
| CN | 106943164 A | 7/2017 | | |
| TW | M306863 U | 3/2007 | | |
| TW | M527307 U | 8/2016 | | |
| TW | M527308 U | 8/2016 | | |
| TW | 201630562 A | 9/2016 | | |
| WO | WO-2015088142 A1 * | 6/2015 | ......... | G02B 23/2476 |

OTHER PUBLICATIONS

Ho et al., "Towards the Development of a Tendon-Driven Neurosurgical Robot," ResearchGate, Jan. 2011, 5 pages total.

Kim et al., "Towards the Development of a Spring-based Continuum Robot for Neurosurgery," Proc. of SPIE, vol. 9415, pp. 94151Q-1-941515Q-6 (7 pages total).

* cited by examiner

MINIMALLY INVASIVE SURGICAL INSTRUMENTS WITH TERMINAL STEERABLE MECHANISM

PRIORITY

The present invention claims priority to the Application No. 106137978 filed on Nov. 2, 2017 in Taiwan (ROC), which was entitled "MINIMALLY INVASIVE SURGICAL INSTRUMENTS WITH TERMINAL STEERABLE MECHANISM". All of which are hereby incorporated by reference as if fully set forth herein.

FIELD OF INVENTION

This invention generally relates to a minimally invasive surgical instrument. Specifically, the present invention relates to a minimally invasive surgical instrument with terminal steerable mechanism.

BACKGROUND

Recently, minimally invasive surgery is becoming more and more popular in the field of clinical medicine since its characteristics of reduced wound area and shortened operation time. However, different instruments might be used in a narrow workspace in common minimally invasive surgery, multiple replacements and insertions of the instruments may unnecessarily increase the operation time and increase the risk of wound infection to the patients.

Otherwise, when the range of lesions is large, medical staffs usually need to remove and reposition the insertion instrument or directly move the insertion instrument in situ to adjust the terminal of the instrument so as to interact with the lesion. Since the lesion is usually located under, over or adjacent to the normal tissue, this step greatly increases the possibility of injuring the patient's normal tissue and may cause unnecessary sequelae. For example, when a surgery of removal of intracranial hematoma or blood clot is performed, such repetitive movement of the above instruments through the normal tissues may increase the risk of damage to the brain.

SUMMARY OF THE INVENTION

Technical Means for Solving the Problems

To solve the above issues, an embodiment of the present invention provides a minimally invasive surgical instrument with terminal steerable mechanism. The minimally invasive surgical instrument comprises an intervention device, a control device and at least one wire. The strip-shaped intervention device sequentially includes a main section, a flexible section and an operation section from the top to the end. The control device includes a sphere with a preset rotational degree of freedom and an operating lever connected to the sphere. Said at least one wire is extended along the main section of the intervention device. In the minimally invasive surgical instrument, a second end of said at least one wire is connected to the flexible section or the operation section of the intervention device, and a first end of said at least one wire is connected to at least a part of the control device.

Technical Effects Achieved by the Technical Means

According to the embodiments of the present invention, a minimally invasive surgical instrument is provided to integrate one or more instruments with various functions. Through the minimally invasive surgical instrument, the end of the instruments inserted in the body can be independently steered. Therefore, the operational convenience for the medical staffs can be improved, and the possibility of injury to the patient during the operation can be decreased.

DETAILED DESCRIPTION OF THE PRESENT INVENTION

Figure 1:
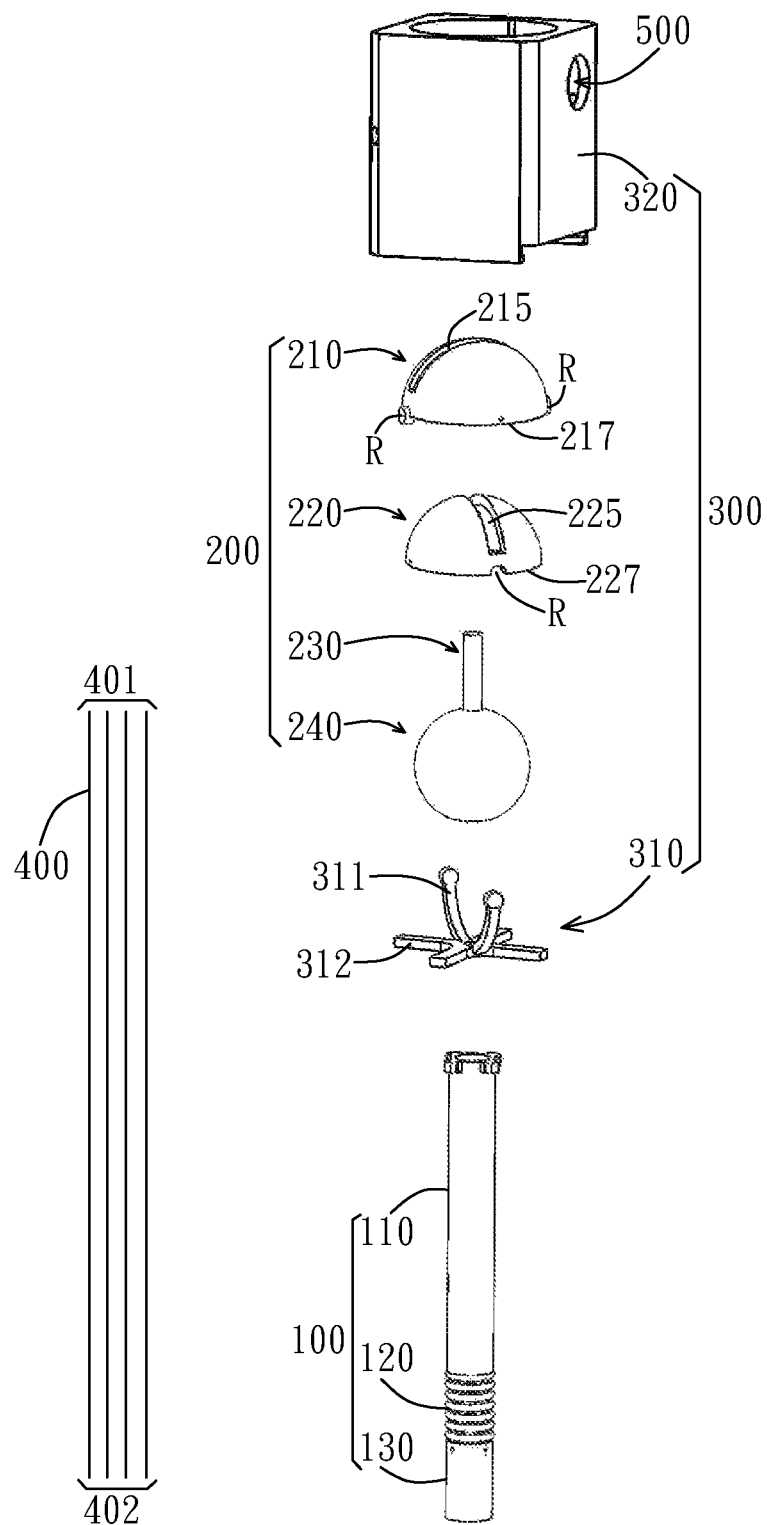
FIG. 1 is an exploded view of a minimally invasive surgical instrument with terminal steerable mechanism according to an embodiment of the present invention.

The present invention will be described more completely hereinafter with reference to the accompanying drawings, in which exemplary embodiments of the invention will be shown. In the drawings, the thickness of layers and regions may be exaggerated or otherwise modified for clarity. The same or similar reference numerals in different drawings represent the same or similar elements. Furthermore, well-known structures, materials, or operations are not shown or described in detail to avoid obscuring aspects of the described devices. As those skilled in the art would realize, the described embodiments may be modified in various different ways, all without departing from the spirit or scope of the present invention. It should be noted that, without conflict, in the embodiment of the present invention and examples of features can be combined with each other. Therefore, it should be appreciated that the embodiments described herein are not intended to be exhaustive of all possible embodiments in accordance with the present disclosure, and that additional embodiments may be conceived based on the subject matter disclosed herein.

Hereinafter, a minimally invasive surgical instrument 10 with terminal steerable mechanism for performing minimally invasive surgery according to an embodiment of the present invention will be described with reference to FIGS. 1 to 2.

Figure 2:
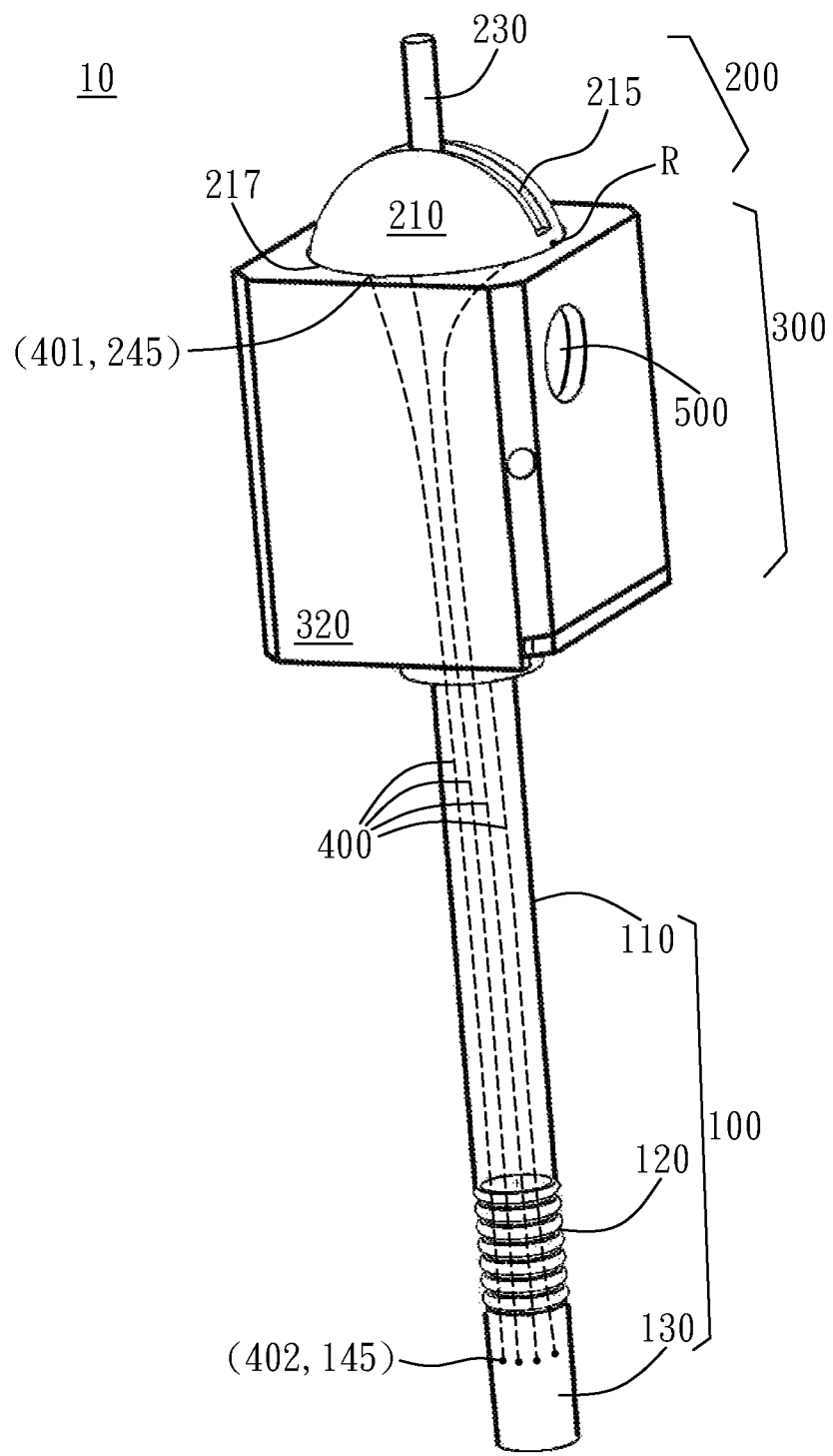
FIG. 2 is a schematic perspective view of a minimally invasive surgical instrument with terminal steerable mechanism according to an embodiment of the present invention.

Referring to FIG. 1 and FIG. 2, the minimally invasive surgical instrument 10 includes an intervention device 100 configured to be inserted into the body of the patients, a control device 200 configured to control the intervention device 100, and one or more wires 400.

In some embodiments, the intervention device 100 can be directly connected to the control device 200 and aligned with the control device 200. Alternatively, in other embodiments, the intervention device 100 can be aligned and assembled with the control device 200 in other ways. For example, as shown in FIG. 1 and FIG. 2, in a preferred embodiment, a positioning device 300 may be utilized to facilitate the alignment and assembly of the intervention device 100 and the control device 200. Specifically, the positioning device 300 may be configured to receive and dispose the control device 200 therein, and fix the top of the intervention device 100 thereon, such that the intervention device 100 is aligned with the control device 200. However, the above is only illustrated as an example, and aspects of the alignment and the assembly of the intervention device 100 and the control device 200 through the positioning device 300 is not limited thereto.

In some embodiments, the structure of the intervention device 100 is presented as strip-shaped. For example, the intervention device 100 itself may be a strip-shaped device with a specific function, and can be operated to perform desired work independently. Moreover, in other embodiments, the intervention device 100 may be tubular hollow, and the interior of the intervention device 100 can be configured to further receive one or more flexible tubular instruments (not shown in FIG. 1 and FIG. 2). Moreover, according to yet another embodiment, the interior of the intervention device 100 may be further separated into different compartments. In such embodiment, each of the compartments can respectively receive different or the same corresponding flexible tubular instruments.

For instance, said flexible tubular instruments can be endoscope, aspiration tube, perfusion tube, clip-shaped device, shearing device, electrocautery device, or any combination thereof. According to an embodiment of the present invention, the flexible tubular instruments such as the endoscope, the aspiration tube and the perfusion tube can be provided in the intervention device 100. Accordingly, the endoscope, the aspiration tube and the perfusion tube can be used to ensure the surgical vision, perform suctioning of the blood and perform perfusion of the surgical area in a surgery, such as a surgery of removal of intracranial hematoma or blood clot in the brain. However, the above is only illustrated as an example, and one, two, three, or more strip-shaped instruments with various functions as the flexible tubular instruments can be received in the intervention device 100. Moreover, apart from the brain surgery, the minimally invasive surgical instrument with terminal steerable mechanism according to various embodiments of the present invention can also be applied to other kinds of minimally invasive surgery. The number, function, and type of the flexible tubular instruments received in the intervention device 100 are arranged accordingly, and the present invention is not limited to the embodiments specifically shown herein.

According to an embodiment, said intervention device 100 sequentially includes a main section 110, a flexible section 120 and an operation section 130 from the top to the end. The main section 110 and the operation section 130 may be an inflexible structure or a structure with limited flexibility, or the main section 110 and the operation section 130 may be made of at least one inflexible material or at least one material with limited flexibility. By contrast, the flexible section 120 may be a structure of corrugated shells, similar to the drinking straws that is flexible, or the flexible section 120 may be other foldable structures or multiple joint structures that is foldable. However, as long as the flexible section 120 is flexible and/or foldable, the present invention is not limited thereto.

Based on the above configuration, the operation section 130 of the intervention device 100 is radially rotatable with respect to the main section 110 of the intervention device 100 by folding and bending the flexible section 120 of the intervention device 100. Accordingly, the terminal end of the intervention device 100 can be independently rotated in a desired direction. According to an embodiment of the present invention, since the one or more flexible tubular instruments is/are extended from the main section 110 to the flexible section 120 and the operation section 130 along the longitudinal length of the intervention device 100, the one or more flexible tubular instruments inside the intervention device 100 can be bent along with the intervention device 100. Thus, the intervention device 100 can guide the terminal end of flexible tubular instruments to a desired position in the desired direction. For example, the endoscope, the aspiration tube and the perfusion tube can be guided to the position of a lesion that is needed to be observed or treated.

In said minimally invasive surgical instrument 10, the control device 200 is mainly configured to control the steering of the operation section 130 at the terminal end of the intervention device 100. Specifically, the control device 200 may include a sphere 240 and an operating lever 230 connected to the sphere 240. The sphere 240 is provided with a preset rotational degree of freedom, and the operating lever 230 can be manipulated to adjust the rotation of the sphere 240 based on the preset rotational degree of freedom of the sphere 240.

Figure 3A:
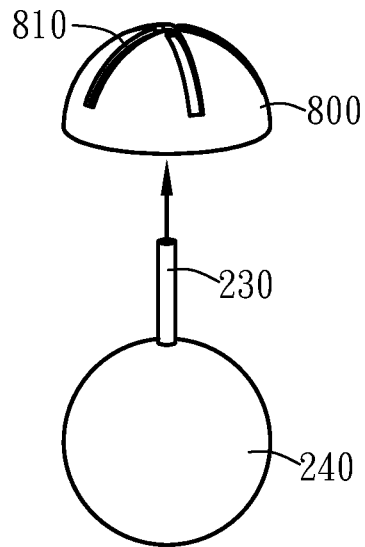
FIG. 3A and FIG. 3B are respectively schematic views of a guide housing and a guide groove of the minimally invasive surgical instrument with terminal steerable mechanism according to different embodiments of the present invention.
Figure 3B:
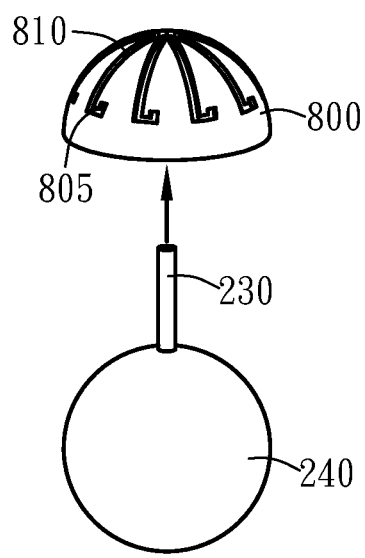

Referring to FIG. 3A and FIG. 3B, according to other embodiments of the present invention, minimally invasive surgical instrument 10 may further include a guide housing 800. The guide housing 800 may be fixed. For example, the guide housing 800 may be fixed at the positioning device 300, but the present invention is not limited thereto. One or more guide grooves 810 in a preset shape may be formed on the guide housing 800 and penetrate the guide housing 800. Accordingly, the guide housing 800 can cover at least a part of the sphere 240 with a gap therebetween, and the operating lever 230 connected to the sphere 240 can penetrate the guide housing 800 and be held in position thereby. In detail, the operating lever 230 can protrude from the guide housing 800 through the guide grooves 810 such that the operating lever 230 is capable of moving along the guide grooves 810. In some embodiments, an operator can thereby adjust the rotation of the sphere 240 by manipulating the movements of the operating lever 230 along the preset shape of each guide groove 810. In this situation, the guide housing 800 remains stationary while the sphere 240 is rotated. That is, the sphere 240 can be rotated independently inside the guide housing 800.

For example, referring to FIG. 3A, a predetermined shape of the guide grooves 810 may be a cross shape, such that the operating lever 230 can be used to adjust the rotation of the sphere 240 by moving within the range of the cross shape. Alternatively, referring to FIG. 3B, a predetermined shape of the guide grooves 810 may be a radial shape, such that the operating lever 230 can be used to adjust the rotation of the sphere 240 by moving within the range of the radial shape. Further referring to FIG. 3B, the guide grooves 810 may include a positioning sub-groove 805. Accordingly, after moving to a desired position along the predetermined shape of the guide grooves 810, the operating lever 230 can be fixed, positioned or hold by the positioning sub-groove 805. However, the design of the guide housing 800 is not limited thereto, and the shape, configuration, or arrangement of the guide grooves 810 are not limited to the above examples. Furthermore, according to some embodiments of the present invention, the guide housing 800 may be alternately a part of the positioning device 300, but the present invention is not limited thereto.

Referring back to FIG. 1 and FIG. 2, according to an embodiment of the present invention, the control device 200 may include a first spherical shell 210 and a second spherical shell 220 with a thin shell-shaped. The first spherical shell 210 and the second spherical shell 220 cover a portion (eg, upper portion) of an outer surface of the sphere 240, and are overlapped with each other.

According to an embodiment, an elongated first groove 215 is formed on the first spherical shell 210, and an elongated second groove 225 is formed on the second spherical shell 220.

Specifically, the first spherical shell 210 and the second spherical shell 220 can be overlapped such that the first groove 215 and the second groove 225 extend crossed with each other according to a predetermined angle. Accordingly, at least a part of the first groove 215 and the second groove 225 apart from intersection of the first groove 215 and the second groove 225 are not overlapped with each other, and edges of the at least a part of the first groove 215 and the second groove 225 are offset with respect to each other. The operating lever 230 may penetrate and protrude out through the overlapped first spherical shell 210 and the second spherical shell 220 at the same time through the first groove 215 and the second groove 225 at the intersection. Therefore, the protruded operating lever 230 can be manipulated by the operator to control the control device 200. Here, the operating lever 230 protruded from the first groove 215 and the second groove 225 can be designed as various shapes and constructions if needed, and the present invention is not limited to the rod shape specifically illustrated in the drawings.

According to a preferred embodiment of the present invention, the first groove 215 and the second groove 225 may intersect perpendicularly with each other. That is, the first groove 215 and the second groove 225 may intersect each other in a predetermined angle of 90 degrees. However, the above is only illustrated as an example, and the present invention is not limited thereto.

In detail, according to an embodiment of the present invention, two predefined points R of the periphery of the first spherical shell 210 corresponding to the two ends of the first groove 215 and two predefined points R of the periphery of the second spherical shell 220 corresponding to the two ends of the second groove 225 can be fixed (as shown in FIG. 1). In detail, the two predefined points R of the first spherical shell 210 are the intersection points of the extension line of the first groove 215 and the periphery 217 of the first spherical shell 210 at two sides of the Centre of the first spherical shell 210. Similarity, the another two predefined points R of the second spherical shell 220 are the intersection points of the extension line of the second groove 225 and the periphery 227 of the second spherical shell 220 at two sides of the Centre of the second spherical shell 220. Here, the predefined points R of the periphery of the first spherical shell 210 and the second spherical shell 220 can be fixed in any manner. In detail, in some embodiments, the positioning device 300 that is optionally set may include a housing 320, and the intervention device 100 may be disposed below the housing 320 and the control device 200 may be relatively positioned at the upper portion of the housing 320. Accordingly, the predefined points R at the peripheries 217 and 227 of the first spherical shell 210 and the second spherical shell 220 can be directly fixed at the housing 320 of the positioning device 300.

Specifically, the two predefined points R of the periphery 217 of the first spherical shell 210 are located corresponding to two ends of the first groove 215 along the longitudinal direction and are fixed at the housing 320 of the positioning device 300, and the two predefined points R of the periphery 227 of the second spherical shell 220 are located corresponding to two ends of the second groove 225 along the longitudinal direction and are fixed at the housing 320 of the positioning device 300. Thus, the overlapped first spherical shell 210 and the second spherical shell 220 can be rotated respectively around the respective rotation axis passing through the respective two predefined points R. That is, the connection line of the two predefined points R can be defined as the rotation axis, and the first spherical shell 210 and the second spherical shell 220 can be independently rotated with respect to each other around the respective rotation axis thereof.

However, the above is only illustrated as an example, and any form or construction that can dispose the top of the intervention device 100, position the control device 200 and fix the predefined points R of the first spherical shell 210 and the second spherical shell 220 can be applied. Moreover, the top of the intervention device 100 may be connected to at least a part of the positioning device 300 (for example, the housing 320) through an intermediate component/intermediate components (not shown). For example, the top of the intervention device 100 may include a specific structure to be wedged in a specific part of the positioning device 300, or the top of the intervention device 100 can be integrally connected to the positioning device 300. Also, the predefined points R of the peripheries 217 and 227 of the first spherical shell 210 and the second spherical shell 220 may be otherwise fixed to other parts of the positioning device 300 other than the housing 320. As explained above, any form or any construction within the scope of the invention can be applied, and the present invention is not limited to the above examples.

Furthermore, referring to FIG. 1 and FIG. 2, the positioning device 300 may include a support frame 310 inside the housing 320. The support frame 310 can be disposed inside the housing 320 and be configured to support and position the sphere 240 so that the sphere 240 is hold in position without dislocation or movement. However, said support frame 310 is not stuck with the sphere 240 in a manner that the sphere 240 cannot rotate. Rather, the sphere 240 is provided with a preset rotational degree of freedom, so that the sphere 240 can rotate while being supported by the support frame 310.

For example, according to an embodiment of the present invention, the support frame 310 may include a cross-shaped fixing frame 312 fixed to the housing 320, and a curved frame 311 fixed to the fixing frame 312. The curved frame 311 holds the sphere 240 to form a ball and socket joint structure. In detail, the peripheral surface of at least a part of the sphere 240 (for example, the lower portion of the sphere 240) can adjoin to and rest against the curved frame 311, such that the curved frame 311 can hold the sphere 240 or define a space to accommodate the sphere 240. In this way, the sphere 240, the first spherical shell 210 and the second spherical shell 220 are provided with a preset rotational degree of freedom, such that the sphere 240, the first spherical shell 210 and the second spherical shell 220 can rotate inside the curved frame 311.

Also, according to a preferred embodiment of the present invention, both ends of the curved frame 311 can be a circular shape that is rounded and smooth, so that the sphere 240, the first spherical shell 210 and the second spherical shell 220 can smoothly rotate. However, the above are only examples. As long as the sphere 240 can be positioned while remaining the preset rotational degree of freedom of the sphere 240, the first spherical shell 210 and the second spherical shell 220, the support frame 310 can have any shape, form and construction. The present invention is not limited to the examples stated herein. For example, the fixing frame 312 can have a non-cross-shaped flat plate shape, and two curved frames 311 can cross each other to become a cross-shaped curved frame so as to further enhance the supporting stability.

Accordingly, based on the stated configuration, the operating lever 230 connected to the sphere 240 and protruded from the first groove 215 and the second groove 225 can respectively slide along one of the first groove 215 and the second groove 225. Therefore, when the operating lever 230 moves along the second groove 225 of the second spherical shell 220, the sphere 240 and the first spherical shell 210 can rotate around the two predefined points R of the first spherical shell 210; and when the operating lever 230 moves along the first groove 215 of the first spherical shell 210, the sphere 240 and the second spherical shell 220 can rotate around the two predefined points R of the second spherical shell 220.

The above stated embodiment of two spherical shells is only illustrated as an example. According to another embodiment of the present invention, the control device 200 may contain only one spherical shell of the first spherical shell 210 to cover a portion of the outer surface of the sphere 240. In the case that only one first spherical shell 210 is provided, the operating lever 230 can directly penetrate the first spherical shell 210 and is protruded from the first spherical shell 210. Also, the two predefined points R of the periphery 217 of the first spherical shell 210 at two sides of the centre of the first spherical shell 210 (for example, the two predefined points R having 180 degrees difference relative to the centre of the first spherical shell 210) can be fixed. Accordingly, the first spherical shell 210 can be provided with a preset rotational degree of freedom around the rotation axis passing through the two predefined points R.

According to an embodiment of the present invention, said one or more wires 400 is/are disposed and extended along the main section 110. The second end 402 of the one or more wires 400 is/are connected to the flexible section 120 or the operation section 130 of the intervention device 100, or is/are connected to the boundary portion between the flexible section 120 and the operation section 130 of the intervention device 100. Meanwhile, the first end 401 of the one or more wires 400 is/are connected to at least a part of the control device 200, such as the sphere 240, the first spherical shell 210, the second spherical shell 220 or the operating lever 230.

According to various embodiments of the present invention, the wires 400 may be relatively tough nylon wires, metal wires, or other wires that is commonly used in the medical surgical instruments, and is not limited thereto.

Specifically, referring to FIG. 2, in one embodiment, the intervention device 100 may include a plurality of connecting holes 145. The connecting holes 145 are distributed along the wall of the intervention device 100 and arranged in a ring shape. The plurality of second ends 402 of the one or more wires 400 can be respectively connected to the corresponding one connecting hole 145. Similarly, the sphere 240, the first spherical shell 210, the second spherical shell 220 or the operating lever 230 may include a plurality of connecting holes 245. The connecting holes 245 are distributed along the periphery of the sphere 240, the first spherical shell 210, the second spherical shell 220 or the operating lever 230 and arranged in a ring shape. The plurality of first ends 401 of the one or more wires 400 can be respectively connected to the corresponding one connecting hole 245. For example, as shown in FIG. 2, the first ends 401 of the one or more wires 400 may be respectively connected to the corresponding connecting holes 245 arranged on the first spherical shell 210 and the second spherical shell 220. However, the arrangement, position, and number of the connecting holes 145 and the connecting holes 245 are not limited to those described in the above embodiments.

In a preferred embodiment, the connecting holes 245 of the corresponding line 400 is not positioned at the non-rotatable predefined points R of the first spherical shell 210 and the second spherical shell 220.

Accordingly, in one embodiment, when the operating lever 230 moves along the first groove 215 of the first spherical shell 210, the sphere 240 and the second spherical shell 220 can rotate; and when the operating lever 230 moves along the second groove 225 of the second spherical shell 220, the sphere 240 and the first spherical shell 210 can rotate. Therefore, as the sphere 240 and one of the first spherical shell 210 and the second spherical shell 220 rotate along with the movement of the operating lever 230, the one or more wires 400 connected to at least a part of the control device 200 are pulled or released together. Thus, the flexible section 120 can be bent correspondingly so as to turn the operation section 130.

According to a preferred embodiment of the present invention, when a sufficient amount of the wires 400 are provided at various points in different directions along the periphery of the components such as the first spherical shell 210, the second spherical shell 220, the sphere 240, the operating lever 230 or the combination thereof, the operation section 130 is provided with a 360 degrees of radial rotational degree of freedom around the flexible section 120 with respect to the main section 110.

According to a preferred embodiment of the present invention, one or more wires 400 may be extended inside the main section 110, so as to reduce the risk of the wires 400 exposed to the outside and contacting the lesion, the affected part or the physiological tissue.

Here, for ease of illustration and clarity, the one or more wires 400 extending in the positioning device 300 and the intervention device 100 are shown in dashed lines.

Figure 3C:
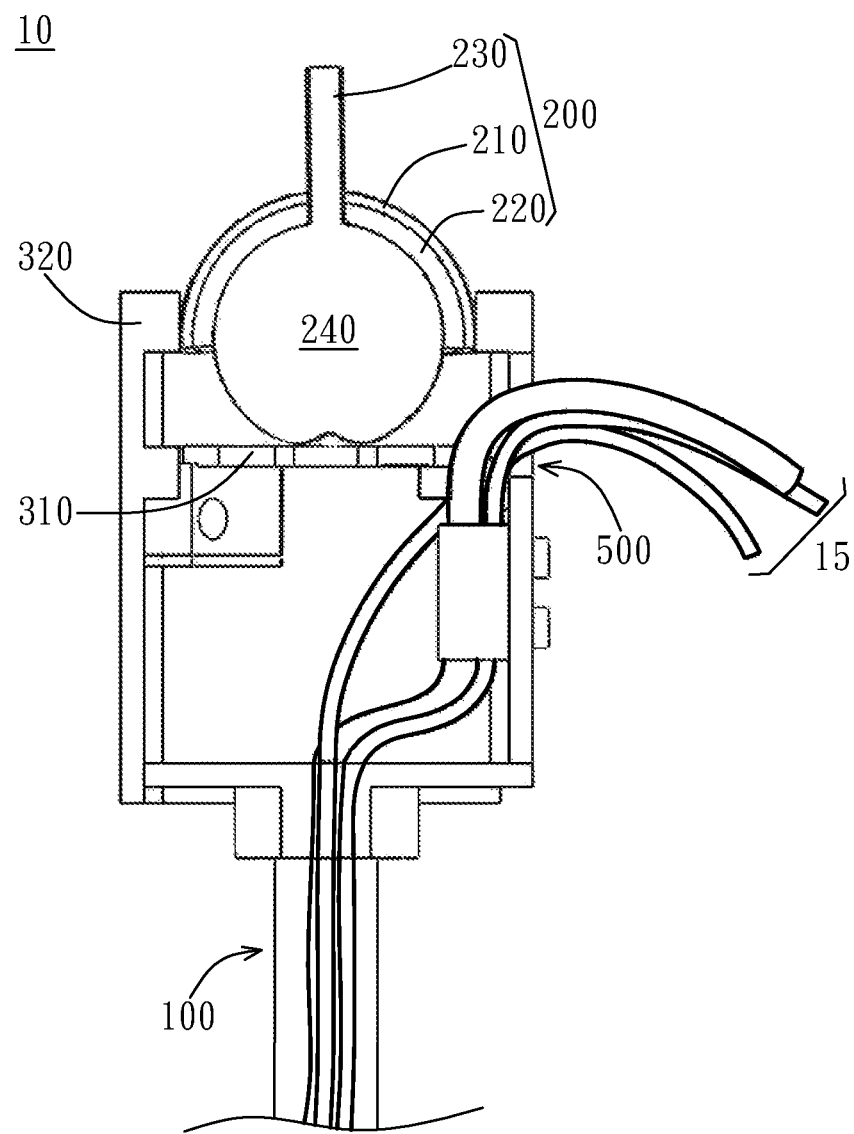
FIG. 3C is a cross-sectional view of a minimally invasive surgical instrument with flexible tubular instruments according to another embodiment of the present invention.

Further, referring to FIG. 3C in connection with FIG. 1 and FIG. 2, according to a preferred embodiment of the present invention, when the intervention device 100 is tubular hollow, one or more flexible tubular instruments 15 can be optionally disposed in the intervention device 100. The flexible tubular instruments 15 may jut out from one or more openings 500 on the sides of housing 320. Here, the configuration, shape, and size of the opening 500 may vary based on the design. However, the detail configuration of the positioning device 300 of the minimally invasive surgical instrument 10 shown in FIG. 3C is only an example, and the present invention is not limited thereto. In addition, the wires 400 are omitted in FIG. 3C for clarity of illustration and to avoid obscuring the description of the flexible tubular instruments 15.

Next, the steering of the operation section 130 described above will be specifically described based on the wire arrangement according to various embodiments of the present invention. In these embodiments, the description will be made by connecting the wires 400 to the first spherical shell 210 and the second spherical shell 220 as an example, but the present invention is not limited thereto.

Figure 4A:
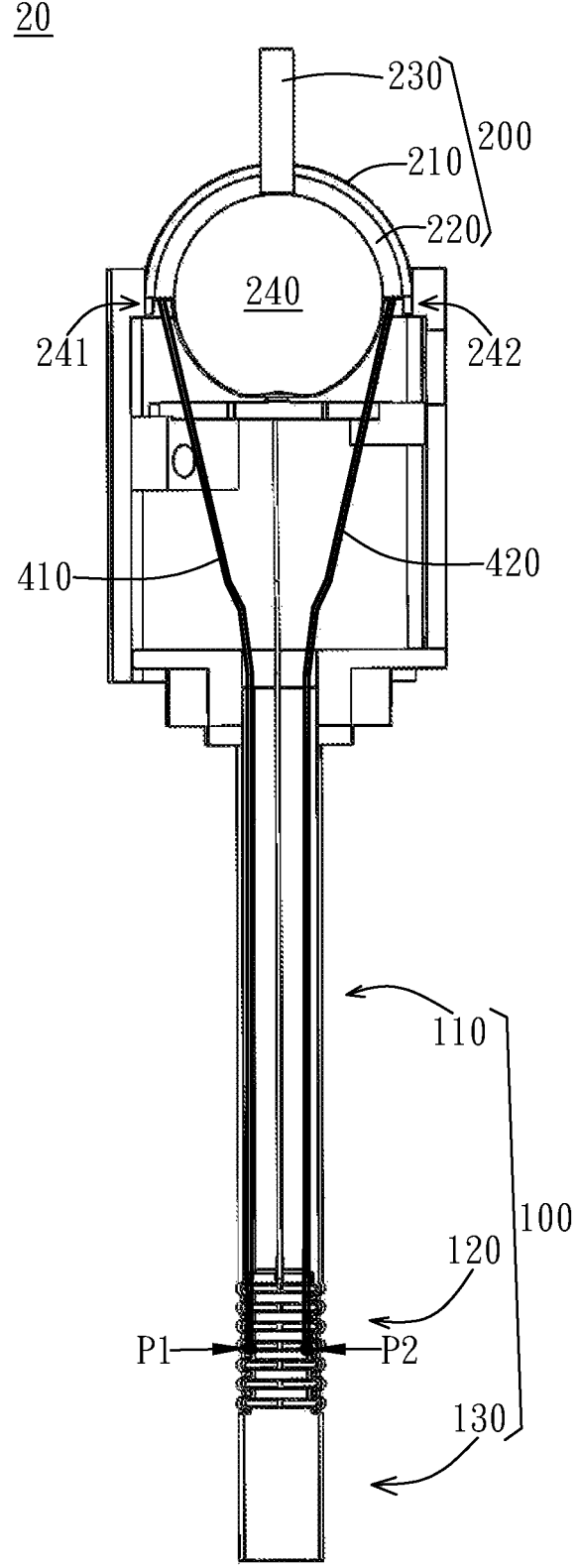
FIG. 4A to FIG. 4C respectively illustrate the steering movement of the operation section of the minimally invasive surgical instrument according to an embodiment of the present invention.
Figure 4B:
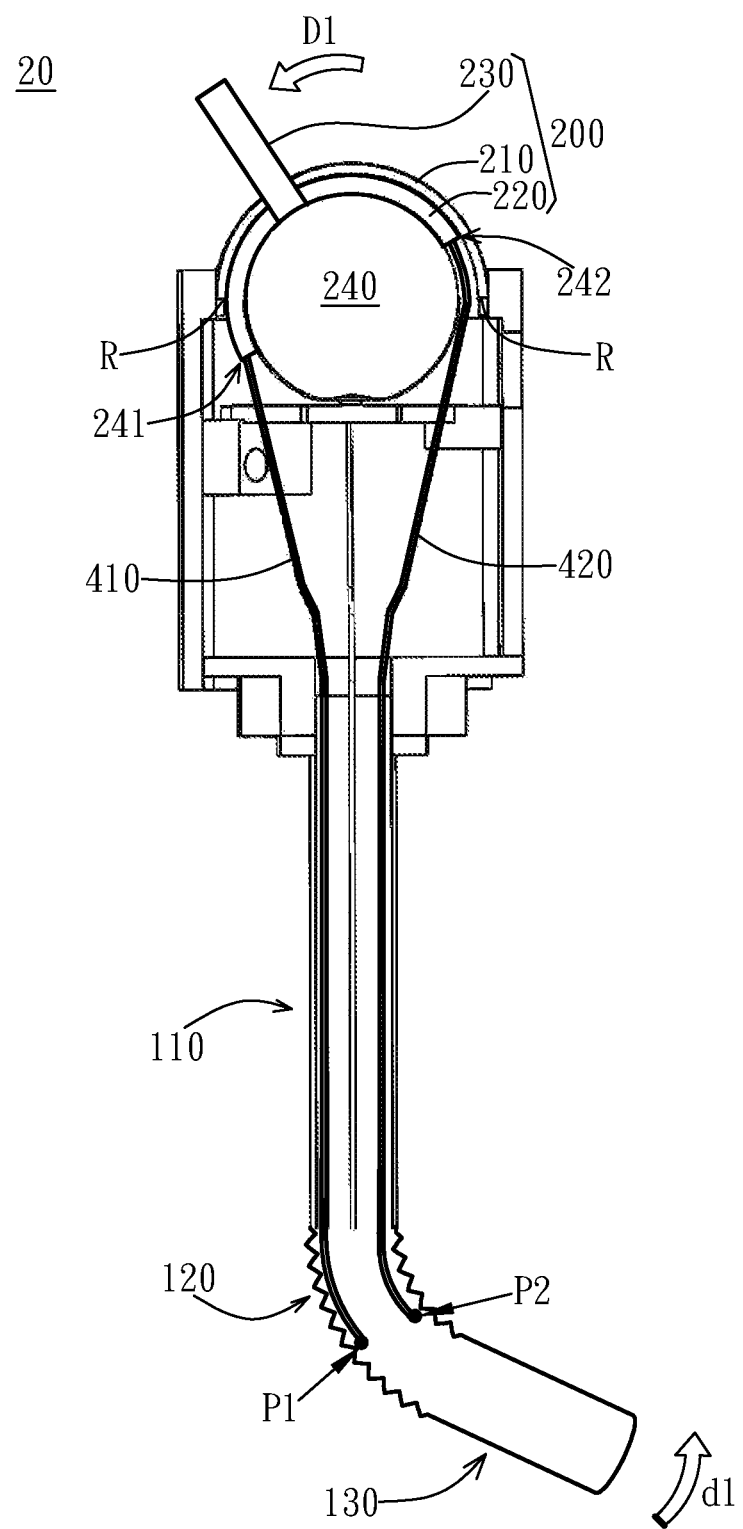
Figure 4C:
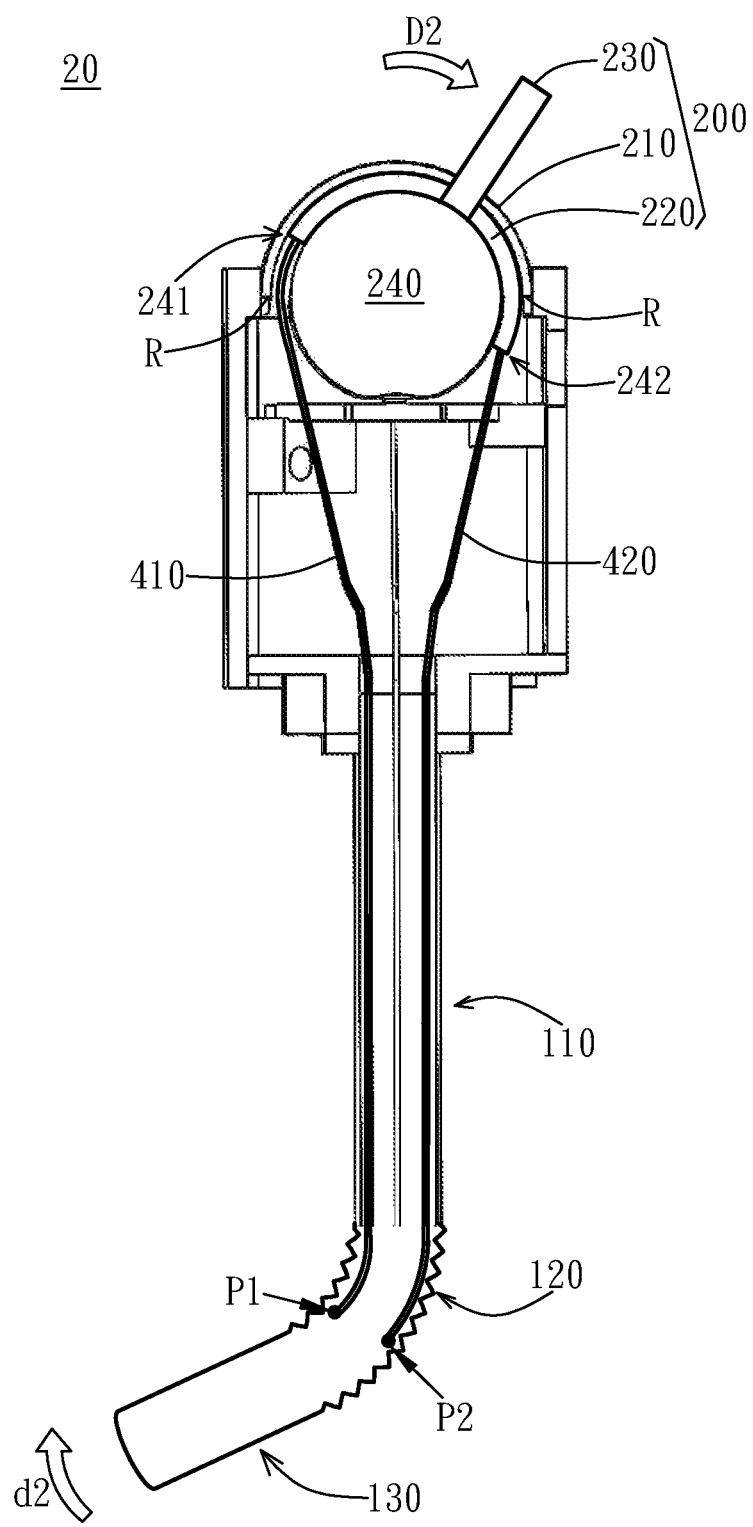

First, referring to the minimally invasive surgical instrument 20 of an embodiment shown in FIG. 4A to FIG. 4C, the first end of the wire 410 may be connected to a positioning point 241 at the edge of the second spherical shell 220, and the second end of the wire 410 may be connected to a positioning point P1 at the flexible section 120. Similarly, the first end of the wire 420 may be connected to a positioning point 242 at the edge of the second spherical shell 220, and the second end of the wire 420 may be connected to a positioning point P2 at the flexible section 120. Here, the positioning point is defined as a specific point located at a predetermined site of the components (such as the second spherical shell 220 or the flexible section 120). Specifically, according to the present embodiment, the positioning point 241 and the positioning point 242 are respectively specific points having 180 degrees difference located at the periphery of the second spherical shell 220. Similarly, the positioning point P1 and the positioning point P2 are respectively specific points having 180 degrees difference located at the inner wall of the flexible section 120. Moreover, the positioning point 241 and positioning point P1 can be located at the same first side with respect to the central axis of the minimally invasive surgical instrument 20, and the positioning point 242 and positioning point P2 can be located at the same second side with respect to the central axis of the minimally invasive surgical instrument 20. In detail, the first side and the second side may have 180 degrees difference relative to the central axis of the minimally invasive surgical instrument 20. However, this is only an example, and the positioning point 241 and the positioning point 242 may be any positions on the edge of the second spherical shell 220 that do not coincide, the positioning point P1 and the positioning point P2 may be any positions on the inner wall of the flexible section 120 that do not coincide, and the present invention is not limited thereto.

In FIG. 4A to FIG. 4C, only two wires connected to the second spherical shell 220 are shown, and other possible wires connected to the second spherical shell 220 and the wires connected to the first spherical shell 210 are omitted for clarity and convenience of explanation.

In contrast to the original state of FIG. 4A, referring to FIG. 4B, when the operating lever 230 connected to the sphere 240 is manipulated to move along the first groove of the first spherical shell 210, the sphere 240 and the second spherical shell 220 can rotate. Specifically, the sphere 240 and the second spherical shell 220 may rotate along the curved frame 311 supporting the sphere 240, and the sphere 240 and the second spherical shell 220 can rotate based on the rotation axis passing through the two predefined points R of the second spherical shell 220. Therefore, the wire 410 and the wire 420 connected to the second spherical shell 220 can be pulled or released along with the rotation of the second spherical shell 220.

In detail, when the operating lever 230 is moved along the longitudinal direction D1 of the first groove towards the first side, the second spherical shell 220 with the second groove that extends crossed with the first groove can be actuated to rotate. Thus, the second spherical shell 220 rotates along direction D1, such that the location of the positioning point 241 changes downward, and the location of the positioning point 242 changes upward.

The length of the wire 410 between the positioning point 241 and the positioning point P1, and the length of the wire 420 between the positioning point 242 and the positioning point P2 are substantially constant. Thus, the lifting of the positioning point 242 leads the positioning point P2 to also elevate accordingly, and the flexible section 120 between the positioning point 242 and the positioning point P2 is compressed. On the contrary, the descent of the positioning point 241 leads the positioning point P1 to also drop accordingly, and the flexible section 120 between the positioning point 241 and the positioning point P1 stretches and releases. Accordingly, due to the compressed and shorten flexible section 120 corresponding to the positioning point P2 at the second side and the stretched and lengthen flexible section 120 corresponding to the positioning point P1 at the first side, the operation section 130 can turn towards the second side along the direction d1.

In contrast, referring to FIG. 4C, when the operating lever 230 is moved along the longitudinal direction D2 of the first groove towards the second side, the second spherical shell 220 with the second groove that extends crossed with the first groove can be actuated to rotate. Thus, the second spherical shell 220 rotates along direction D2, such that the location of the positioning point 241 changes upward, and the location of the positioning point 242 changes downward. Thus, the fixed length wires 410 and 420 are pulled or released. Accordingly, due to the stretched and lengthen flexible section 120 corresponding to the positioning point P2 at the second side and the compressed and shorten flexible section 120 corresponding to the positioning point P1 at the first side, the operation section 130 can turn towards the first side along the direction d2.

It should be noted that the above configuration and movement described with reference to FIG. 4A to FIG. 4C is only illustrated as an example, and the wires can be fixed and actuated in other ways apart from the embodiment of FIG. 4A to FIG. 4C. For example, referring to another embodiment of the minimally invasive surgical instrument 30 shown in FIG. 4D to FIG. 4F, the direction of the movement of the operating lever 230 and the direction of Steering of the operation section 130 are the same for intuitive operation. Specifically, in FIG. 4D to FIG. 4F, the first end of the wire 410 may be connected to a positioning point 241 at the edge of the second spherical shell 220, and the second end of the wire 410 may be connected to a positioning point P2 at the flexible section 120. Similarly, the first end of the wire 420 may be connected to a positioning point 242 at the edge of the second spherical shell 220, and the second end of the wire 420 may be connected to a positioning point P1 at the flexible section 120. Accordingly, in contrast to the original state of FIG. 4D, referring to FIG. 4E and FIG. 4F, when the operating lever 230 is manipulated to move, the direction of the steering of the operation section 130 is the opposite to the above embodiment shown and described with reference to FIG. 4A to FIG. 4C.

Figure 4D:
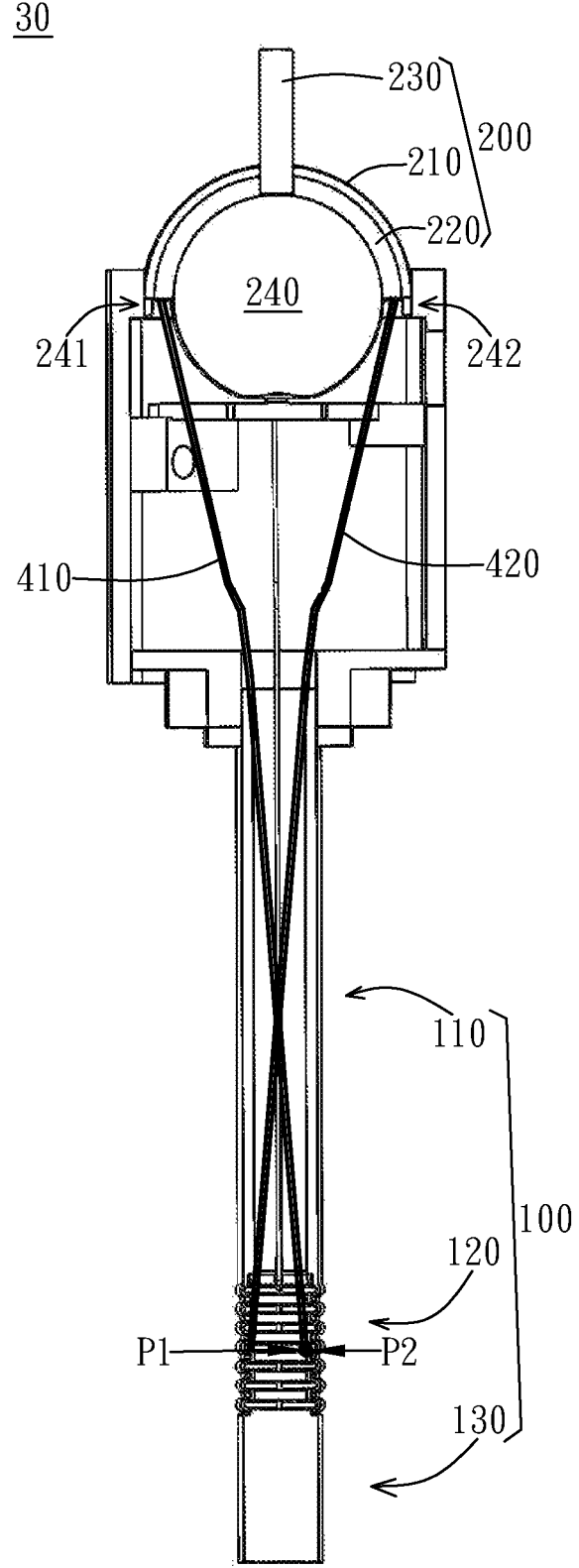
FIG. 4D to FIG. 4F respectively illustrate the steering movement of the operation section of the minimally invasive surgical instrument according to another embodiment of the present invention.
Figure 4E:
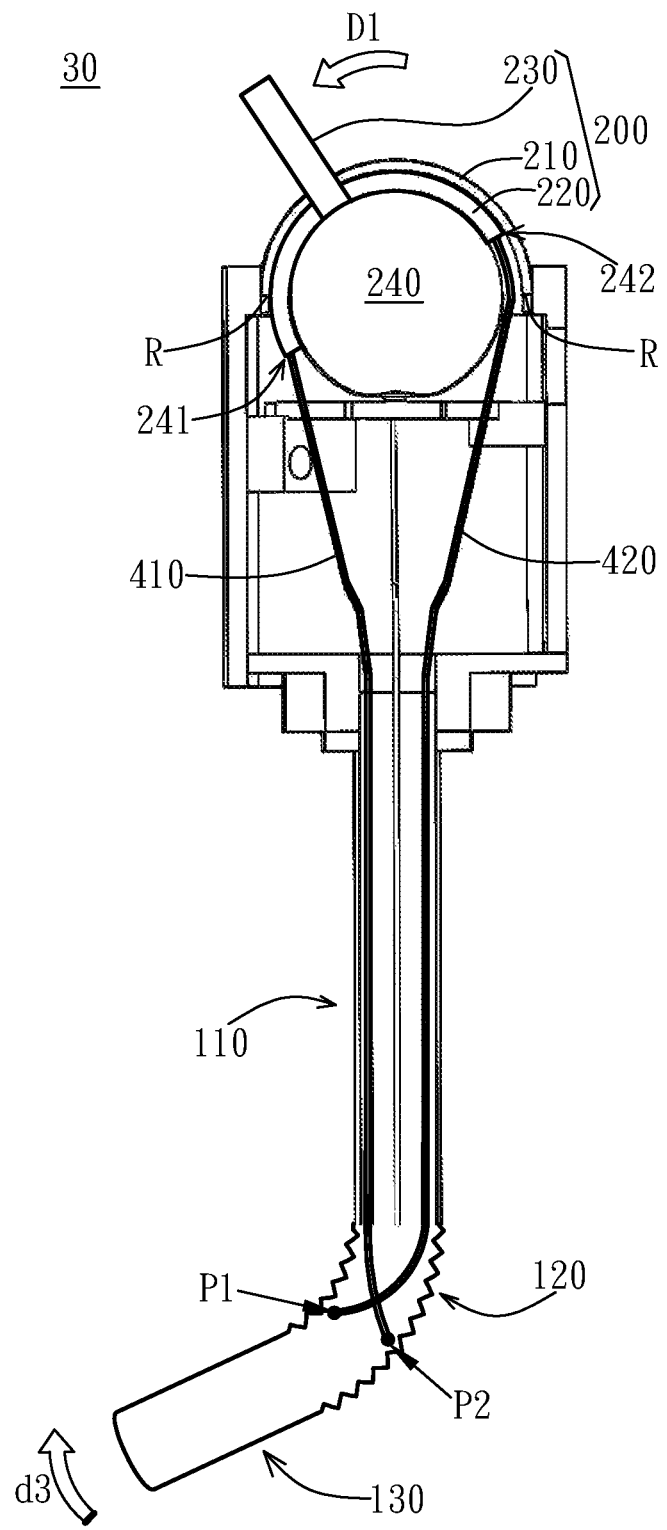

In detail, in contrast to the original state of FIG. 4D, referring to FIG. 4E, when the operating lever 230 is moved along the longitudinal direction D1 of the first groove towards the first side, the second spherical shell 220 with the second groove that extends crossed with the first groove can be actuated to rotate. Thus, the second spherical shell 220 rotates along direction D1, such that the location of the positioning point 241 changes downward, and the location of the positioning point 242 changes upward. Thus, the fixed length wires 410 and 420 are pulled or released, and different portions of the flexible section 120 are pulled or released by the fixed length wires 410 and 420. Accordingly, clue to the compressed and shorten flexible section 120 corresponding to the positioning point P1 at the first side and the stretched and lengthen flexible section 120 corresponding to the positioning point P2 at the second side, the operation section 130 can turn towards the first side along the direction d3.

Figure 4F:
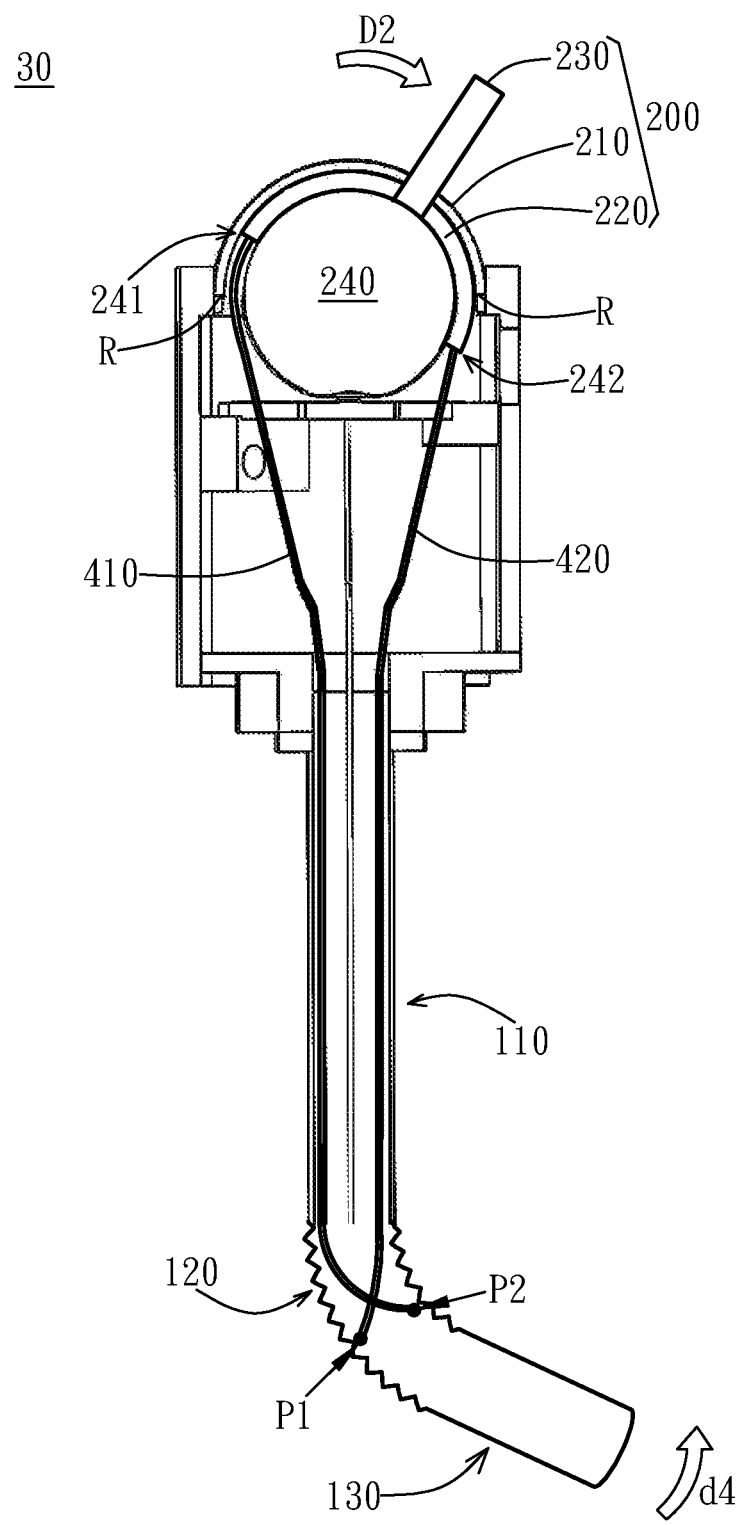

In contrast, referring to FIG. 4F, when the operating lever 230 is moved along the longitudinal direction D2 of the first groove towards the second side, the second spherical shell 220 with the second groove that extends crossed with the first groove can be actuated to rotate. Thus, the second spherical shell 220 rotates along direction D2, such that the location of the positioning point 241 changes upward, and the location of the positioning point 242 changes downward. Thus, the fixed length wires 410 and 420 are pulled or released. Accordingly, due to the compressed and shorten flexible section 120 corresponding to the positioning point P2 at the second side and the stretched and lengthen flexible section 120 corresponding to the positioning point P1 at the first side, the operation section 130 can turn towards the second side along the direction d4.

As described above, according to the minimally invasive surgical instrument 30 shown in FIGS. 4D to 4F, the operating lever 230 can be manipulated by the operator in a relatively intuitive manner. Specifically, the steering direction of the operation section 130 can be controlled by manipulating the movement of the operating lever 230 in the same direction. However, the present invention is not limited thereto, and the minimally invasive surgical instrument can be configured in any manipulation manner to control the steering of the operation section 130 based on the configuration of the components (such as the operating lever 230) according to various usage patterns.

Next, similar to the above situation, when the operating lever 230 is moved along the second groove of the second spherical shell 220, the sphere 240 rotates in the space defined by the support frame 310, and the first spherical shell 210 rotates around the rotation axis passing through the two predefined points R of the first spherical shell 210. Accordingly, the wires (not shown) connected to the first spherical shell 210 are pulled and released along with the rotation of the first spherical shell 210. Apart from the directionality, the process and the working principle of the rotation of the first spherical shell 210 and the corresponding steering of the operation section 130 is substantially the same with the rotation of the second spherical shell 220 and the corresponding steering of the operation section 130 as described with reference to FIG. 4A to FIG. 4F. Thus, the detail description and illustration is not repeated here.

Further, according to one embodiment of the present invention, two wires connected to the first spherical shell 210 and two wires connected to the second spherical shell 220 can be provided. Therefore, the control of the steering can be achieved by such configuration of four wires. However, the present invention is not limited thereto, and the wires can be arranged in various manner in accordance with the demands, the desired operational convenience and the usage patterns. Thus, the steering of the operation section 130 can be achieved when the wires are pulled/released by manipulating the operating lever 230 according to a desire manner.

Figure 5:
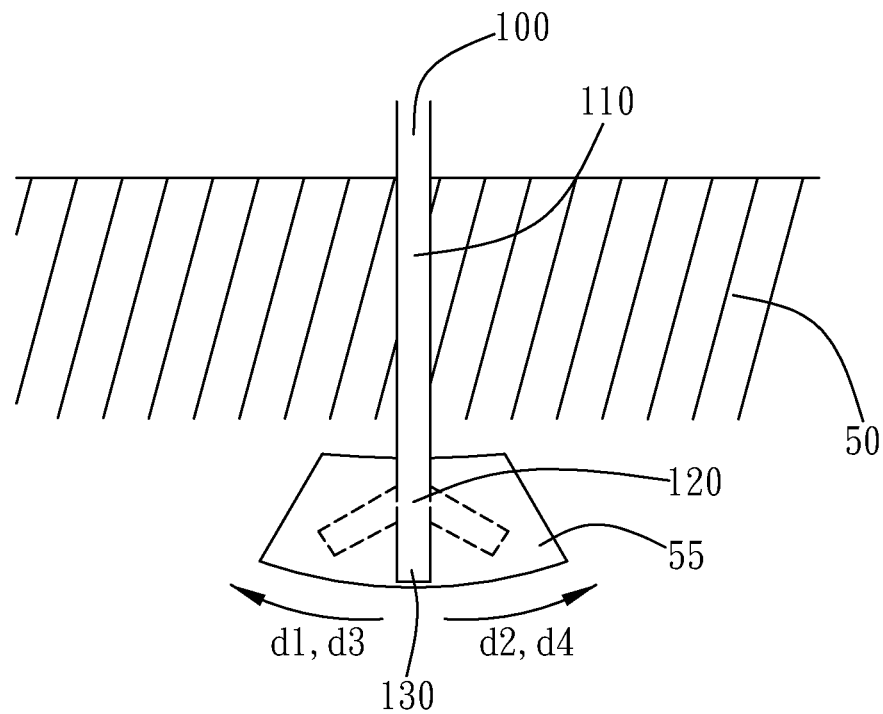
FIG. 5 is a schematic view of a minimally invasive surgical instrument configured to observe, contact or treat the lesion or the predetermined part of the patient in vivo according to various embodiments of the present invention.

As described above, referring to FIG. 5, in the minimally invasive surgical instrument according to the embodiments of the present invention, when the intervention device 100 reaches into the lesion or the predetermined part 55 that is needed to be observed, contacted or treated, the steering of the terminal operation section 130 of the intervention device 100 can be adjusted independently with respect to the main section 110. Specifically, the steering of the terminal operation section 130 inside the body can be adjusted independently by controlling from the outside, such that the normal or non-predetermined part 50 inside the body is not affected or is affected slightly. In detail, for the adjustment of the terminal operation section 130, it is not necessary to take out the inserted intervention device 100 inside the body and reinsert the intervention device 100, or to adjust the inserted angle of the upper portion of the intervention device 100 (that is, the main section 110) inside the body. Therefore, by the minimally invasive surgical instrument with terminal steerable mechanism according to the embodiments of the present invention, the observation, the contact or the treatment of the other part of the lesion or the predetermined part 55 can be employed in a safer way. Accordingly, the area of the lesion or the predetermined part 55 capable to be observed, contacted or treated is increased in the minimally invasive surgery. Thereby, the convenience of the operation for the medical staffs is improved, the operation time for surgery is decreased, and the possible contact and injury to normal or non-predetermined part 50 is reduced.

Here, for example, the lesion or the predetermined part 55 may be a blood clot or hemorrhage in the brain, and the normal or non-predetermined part 50 may be a normal tissue in the brain (such as the cerebral cortex). However, the present invention is not limited thereto. The minimally invasive surgical instrument with terminal steerable mechanism according to the embodiments of the present invention can be used in any minimally invasive surgery. Especially, in the minimally invasive surgery that requires minimal damage to the adjacent portion in vivo.

Moreover, according to a preferred embodiment of the present invention, since the minimally invasive surgical instrument is designed as a relatively simple mechanical mechanism without any electronic device, the minimally invasive surgical instrument may be a disposable medical appliance in the surgery. For example, one or more disposable preset surgical tools (such as the flexible tubular instruments 15) can be provided inside the intervention device 100, and the minimally invasive surgical instrument including the surgical tools can be sterilized so as to be used in the minimally invasive surgery and then discarded. In this way, the risk of the infection that is possibly caused by the repeated use of instruments can be reduced when using the minimally invasive surgical instrument. In this case, the minimally invasive surgical instrument may further include a control valve or a control panel, so as to operate the surgical tools (for example, the switches of the surgical tools can be integrated on the control valve or the control panel on the minimally invasive surgical instrument).

Also, according to other embodiments of the present invention, one or more surgical tools (such as the flexible tubular instruments 15) received in the minimally invasive surgical instrument may be connected to an external counterpart device or equipment. Thereby, the applicability of the minimally invasive surgical instrument can be further expanded. For example, one or more surgical tools can be extended from the minimally invasive surgical instrument to connect with LCD displays, suction pumps, infusion pumps, etc., which are commonly used in surgery. However, the present invention is not limited thereto.

Next, a modified embodiment of the present invention will be further described with reference to FIG. 6 to FIG. 10. In this embodiment, a mistake-proofing mechanism is further provided in the minimally invasive surgical instrument. Accordingly, when the operation section 130 at the terminal of the intervention device 100 turns relative to the main section 110, the medical staffs are prevented from directly taking out the minimally invasive surgical instrument from the body.

Figure 8:
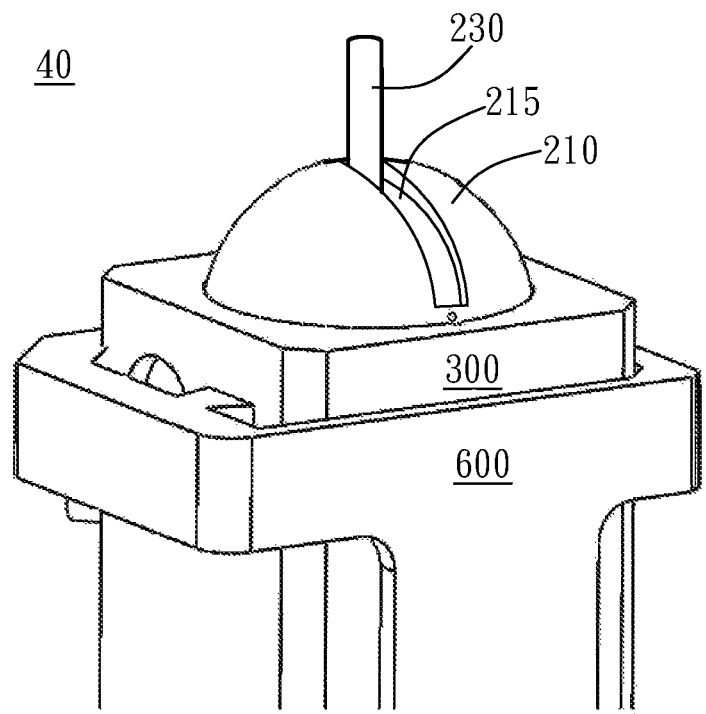
FIG. 8 is a lateral view of an upper portion of the minimally invasive surgical instrument in the initial state according to a modified embodiment of the present invention.

In detail, according to a modified embodiment of the present invention, the positioning device 300 of the minimally invasive surgical instrument 40 may be further fixed by a fixing device 600 having a shape of a case (shown in FIG. 8). In detail, the positioning device 300 can be accommoated and positioned in the fixing device 600. Accordingly, the positioning device 300 of the minimally invasive surgical instrument 40 can be assembled on the fixing device 600 or be disassembled from the fixing device 600, and this will be further described hereinafter. However, the above is only illustrated as an example, and any other part of the minimally invasive surgical instrument 40 can be assembled on the fixing device 600 or be disassembled from the fixing device 600.

Figure 6:
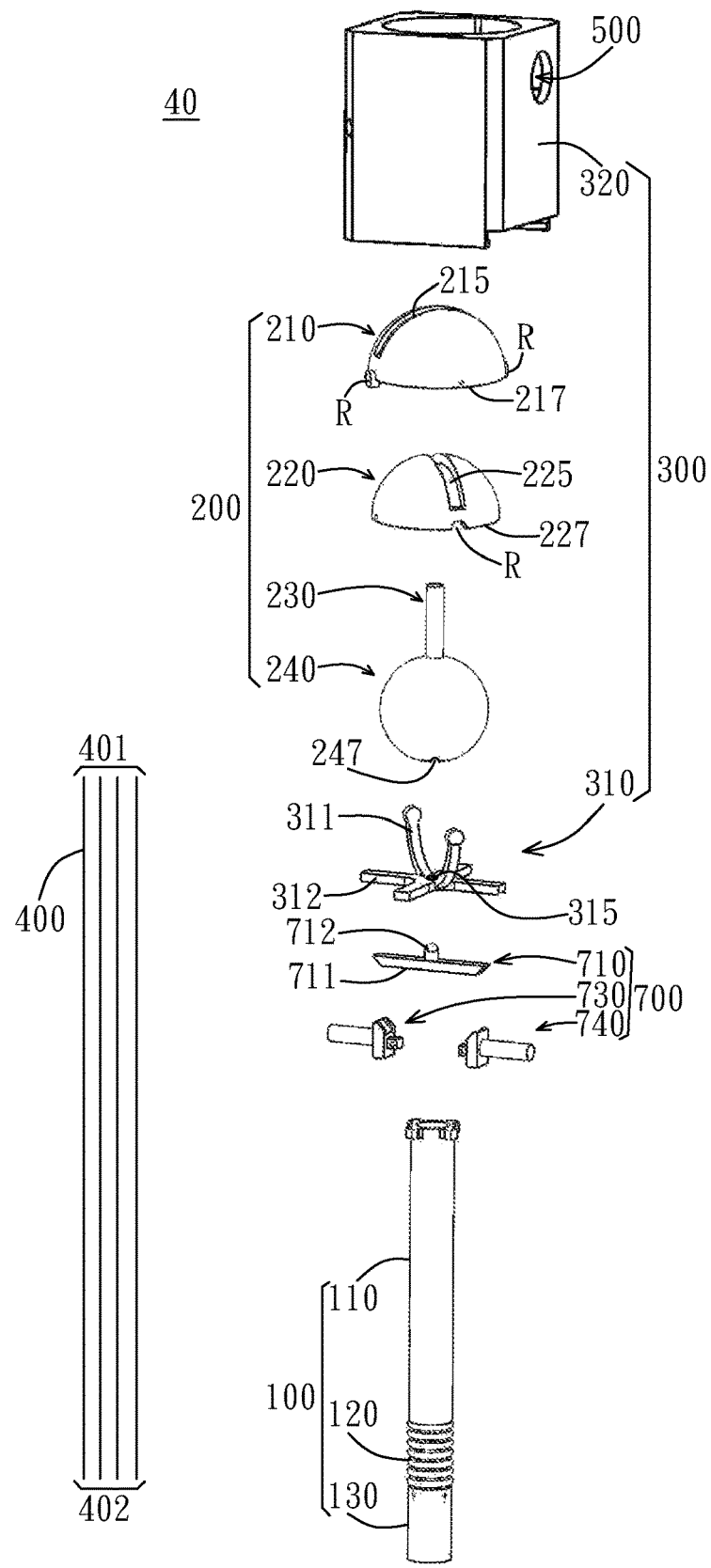
FIG. 6 is an exploded view of a minimally invasive surgical instrument with terminal steerable mechanism according to a modified embodiment of the present invention.

Next, referring to FIG. 6, the minimally invasive surgical instrument 40 may further include a mistake-proofing device 700 compared to the embodiment of FIG. 1. Here, apart from the difference relative to the fixing device 600 and the mistake-proofing device 700, the embodiment of the minimally invasive surgical instrument 40 is substantially the same as the embodiment of the minimally invasive surgical instrument 10 shown in FIG. 1. Thus, the same or similar construction or description of the minimally invasive surgical instrument 40 as the minimally invasive surgical instrument 10 shown in FIG. 1 will be omitted.

Specifically, the mistake-proofing device 700 includes a base portion 710 and one or more latch portions. For example, in one embodiment shown in FIG. 6 to FIG. 10, two latch portions 730 and 740 may be respectively provided at two sides of the base portion 710. However, the present invention is not limited thereto, and only one latch portion or more than three latch portions may be further provided. Specifically, the base portion 710 may include a trunk 711 and a protrusion 712 protruding from the trunk 711, and the protrusion 712 may protrude toward the sphere 240. According to one embodiment, the trunk 711 shown in FIG. 6 to FIG. 10 may have a rod shape. However, the present invention is not limited thereto, and the trunk 711 may have a disk, a rectangle, a polygon, or an irregular shape, and the one or more latch portions may be disposed with respect to the trunk 711.

Figure 7:
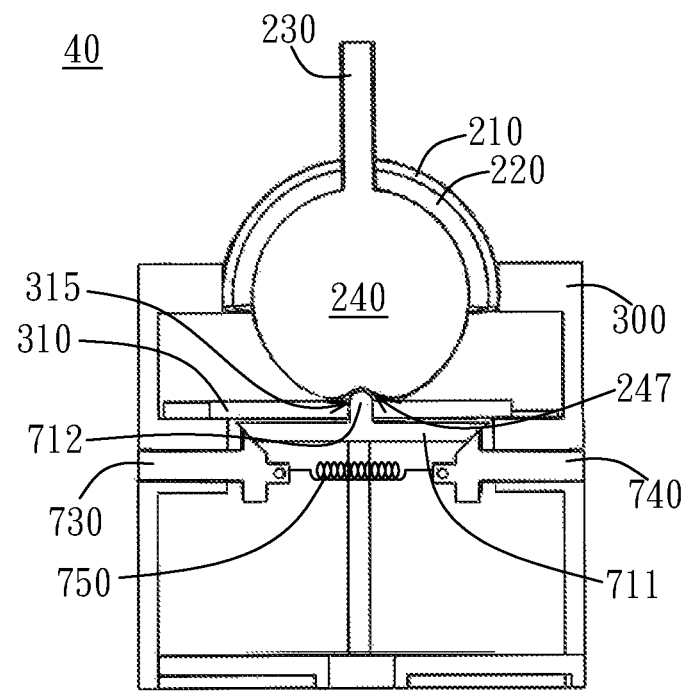
FIG. 7 is a cross-sectional view of an upper portion of the minimally invasive surgical instrument in the initial state according to a modified embodiment of the present invention.
Figure 9:
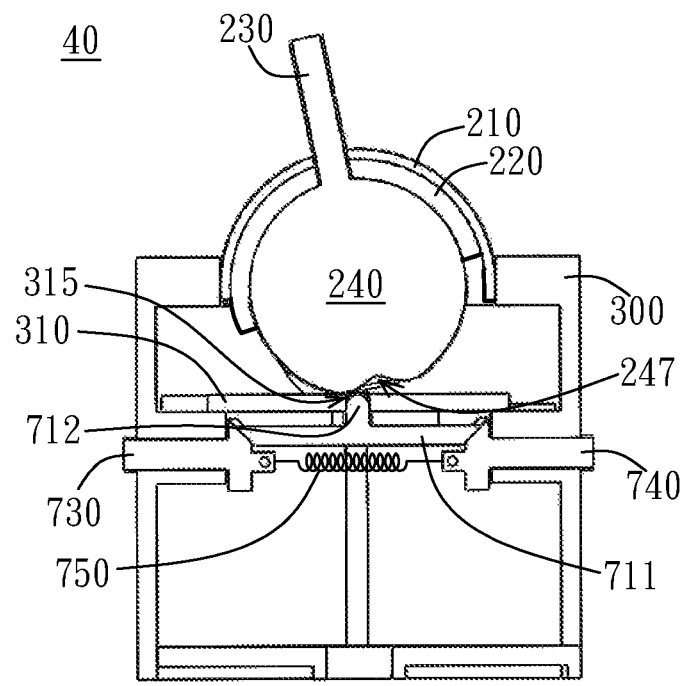
FIG. 9 is a cross-sectional view of an upper portion of the minimally invasive surgical instrument in the steering state according to a modified embodiment of the present invention.

As shown in FIG. 7 and FIG. 9, the protrusion 712 of the base portion 710 may pass through a hole 315 at the centre of the support frame 310 to face and get close to/contact with the sphere 240. However, this is only illustrated as an example, and protrusions according to other embodiments may otherwise bypass the support frame from the side of the support frame to face and get close to/contact with the sphere 240. Thus, the present invention is not limited thereto.

Next, referring to FIG. 7 to FIG. 10 illustrating the operation process of the minimally invasive surgical instrument 40, the cooperative action between the mistake-proofing device 700 and the fixing device 600 according to a modified embodiment will be further described in detail. Here, please note that the fixing device 600 is shown only in FIG. 8 and FIG. 10 for the sake of brevity and convenience.

In detail, referring to the partial cross-sectional view of the minimally invasive surgical instrument 40 of FIG. 7 and the partial lateral view of the minimally invasive surgical instrument 40 of FIG. 8, in the initial state before the sphere 240 rotates so that the intervention device is not bent, the protrusion 712 can be substantially received in a notch 247 of a portion (such as a lower portion) of the sphere 240. Accordingly, the base portion 710 moves upward without pushing the two latch portions 730 and 740, so that the two latch portions 730 and 740 do not protrude from the positioning device 300 of the minimally invasive surgical instrument 40.

Figure 10:
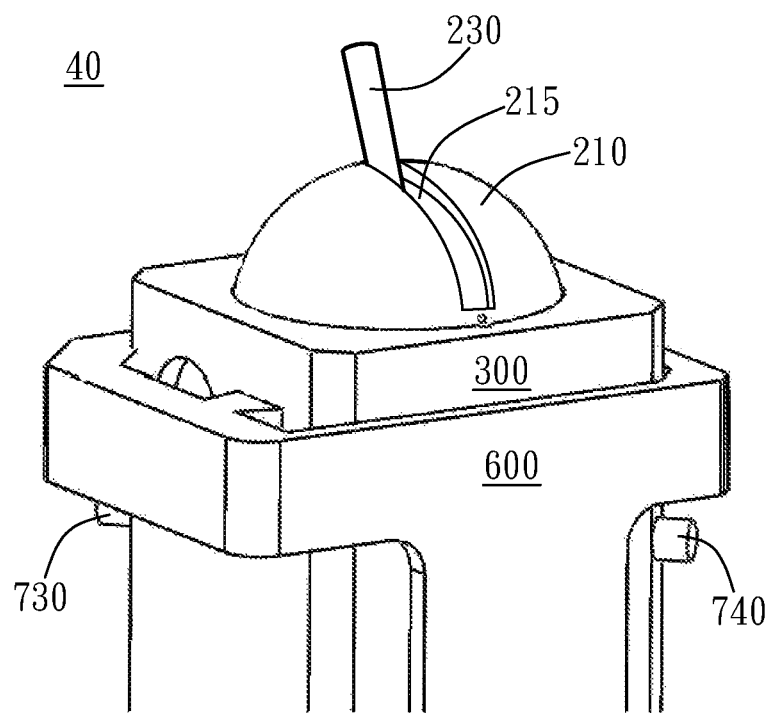
FIG. 10 is a lateral view of an upper portion of the minimally invasive surgical instrument in the steering state according to a modified embodiment of the present invention.

In contrast, referring to the partial cross-sectional view of the minimally invasive surgical instrument 40 of FIG. 9 and the partial lateral view of the minimally invasive surgical instrument 40 of FIG. 10, in the steering state that the sphere 240 rotates and the operation section of the intervention device turns (as described with reference to FIG. 4A to FIG. 4F), the notch 247 deviates from the protrusion 712. Thus, the protrusion 712 of the base portion 710 is pushed downward by the sphere 240, and the trunk 711 of the base portion 710 moves downward accordingly. Thereby, the shifted trunk 711 can push the two latch portions 730 and 740 respectively toward two sides, so the two latch portions 730 and 740 can respectively protrude from the positioning device 300 of the minimally invasive surgical instrument 40. In this way, the positioning device 300 of the minimally invasive surgical instrument 40 can be engaged and fixed with the fixing device 600.

Furthermore, one or more elastic members 750 can be provided. Specifically, the elastic member 750 is configured to press or pull said one or more latch portions in the initial state, so as to prevent said one or more latch portions from getting stuck with the fixing device 600 in the initial state. For example, referring to FIGS. 7 and 9, the two latch portions 730 and 740 may be connected with each other by an elastic member 750 (eg, a spring). Therefore, when the minimally invasive surgical instrument 40 is switched back to the initial state from the steering state, the two latch portions 730 and 740 can be reset to the original position without engaging the fixing device 600.

In addition, according to a preferred embodiment of the present invention, the latch portion and the end of the trunk 711 of the base portion 710 that are in contact with each other can be designed accordingly, so that the latch portion and the end of the trunk 711 can match with each other. For example, the end portion of the two latch portions 730 and 740 that is in contact with the trunk 711 may be formed as a slanted chute structure, and the end portion of the trunk 711 that is in contact with the two latch portions 730 and 740 may be formed as a corresponding slanted tenon structure. Therefore, the corresponding slanted tenon structure can be fitted into the slanted chute structure and slide along the slanted chute structure. However, the above is only an example, and the present invention is not limited thereto.

Based on the above configuration, when the minimally invasive surgical instrument 40 is in the initial state that the intervention device is not bent, the operator can dissemble the positioning device 300 of the minimally invasive surgical instrument 40 from the fixing device 600; and when the minimally invasive surgical instrument 40 is in the steering state that the intervention device is bent, the positioning device 300 of the minimally invasive surgical instrument 40 can be engaged with the fixing device 600, so as to prevent the positioning device 300 of the minimally invasive surgical instrument 40 from being disassembled from the fixing device 600. Therefore, a risk of damaging the body can be decreased. In detail, in the steering state that the terminal end of the minimally invasive surgical instrument 40 is bent, the bent terminal end will injure the normal or non-predetermined part adjacent to the lesion or the predetermined part when the minimally invasive surgical instrument 40 is directly pulled out from the body due to the carelessness or accident of the operator. Thus, the above mistake-proofing mechanism can prevent the accident that the minimally invasive surgical instrument 40 is directly taken out from the body when the minimally invasive surgical instrument 40 is in the steering state, such that the risk of damaging the body can be decreased.

In sum, in the minimally invasive surgical instruments with terminal steerable mechanism according to various embodiments of the present invention, the directionality of the operation section of the minimally invasive surgical instrument inserted in the body at the end can be intuitively adjusted by the operating lever from outside based on the mechanical structure. Therefore, the operation time can be decreased, the convenience of the operation can be improved, and the possibility of injuring the other part of the body in the patient can be reduced. Moreover, based on the minimally invasive surgical instruments according to various embodiments of the present invention, various tools can be integrated into the minimally invasive surgical instrument, thereby increasing the applicability and the versatility of the minimally invasive surgical instruments in the minimally invasive surgery. Also, the relatively simple mechanical mechanism design for terminal steering control can reduce the cost for manufacturing the minimally invasive surgical instruments, and/or reduce the volume, the weight and the complexity of the minimally invasive surgical instruments. Thus, it is easier for the operator to learn the operational skill of the minimally invasive surgical instruments according to the present invention, and the flexibility of the minimally invasive surgical instruments according to the present invention on the clinical application can be improved.

Although the present invention has been described with reference to the preferred embodiments thereof, it will be understood that the invention is not limited to the details thereof. Various changes and modifications in accordance with the appropriate technical solutions and technical concepts of the present invention should belong to the invention as claimed. Therefore, all such substitutions and modifications are intended to be embraced within the scope of the invention as defined in the appended claims.

What is claimed is:
1. A minimally invasive surgical instrument with terminal steerable mechanism, comprising:
  a strip-shaped intervention device sequentially including a main section, a flexible section and an operation section from top to end,
  a control device, including:
    a sphere with a preset rotational degree of freedom;
    an operating lever connected to the sphere; and
    at least one spherical shell covering a portion of an outer surface of the sphere, wherein the operating lever penetrates and protrudes out through the at least one spherical shell, two predefined points of the periphery of the at least one spherical shell are fixed, and the at least one spherical shell is provided with a preset rotational degree of freedom around a rotation axis passing through the two predefined points, and
  at least one wire extended along the main section of the intervention device,
  wherein, a second end of the at least one wire is connected to the flexible section or the operation section of the intervention device, and a first end of the at least one wire is connected to the periphery of the at least one spherical shell that is not fixed.
2. The minimally invasive surgical instrument according to claim 1, further comprising a guide housing covering at least a part of the sphere with a gap therebetween, wherein:
  the guide housing remains stationary while the sphere is rotated, at least one guide groove is formed on the guide housing and penetrates the guide housing,
  the operating lever protrudes from the guide housing through the guide grooves.
3. The minimally invasive surgical instrument according to claim 1, wherein the at least one spherical shell includes a first spherical shell covering a portion of the outer surface of the sphere, and the operating lever penetrates and protrudes out through the first spherical shell, wherein:
  two predefined points of the periphery of the first spherical shell are fixed, and the first spherical shell is provided with a preset rotational degree of freedom around a rotation axis passing through the two predefined points, in which
  the two predefined points are located at two sides of a centre of the first spherical shell.
4. The minimally invasive surgical instrument according to claim 1, wherein the two predefined points have 180 degrees difference relative to the centre of the at least one spherical shell.
5. The minimally invasive surgical instrument according to claim 1, wherein the at least one spherical shell includes a first spherical shell covering a portion of the outer surface of the sphere and a second spherical shell covering a portion of the outer surface of the sphere and overlapped with at least a part of the first spherical shell, wherein:
  a first groove is formed on the first spherical shell and penetrating the first spherical shell;
  a second groove is formed on the second spherical shell and penetrating the second spherical shell; and
  the first groove and the second groove extend crossed with each other, such that at least a part of the first groove and the second groove apart from intersection of the first groove and the second groove are not overlapped with each other, wherein the operating lever penetrates and protrudes out through the first spherical shell and the second spherical shell that are overlapped with each other at the same time through the first groove and the second groove at the intersection;
  wherein the two predefined points of the periphery of the first spherical shell are located corresponding to two ends of the first groove along a longitudinal direction, and another two predefined points of the periphery of the second spherical shell that are fixed are located corresponding to two ends of the second groove along a longitudinal direction.

6. The minimally invasive surgical instrument according to claim 1, wherein the operation section is provided with a 360 degrees of radial rotational degree of freedom around the flexible section with respect to the main section.

7. The minimally invasive surgical instrument according to claim 1, wherein the intervention device includes a plurality of connecting holes distributed along a wall of the intervention device, and the second ends of the wires are respectively connected to the connecting holes.

8. The minimally invasive surgical instrument according to claim 1, wherein the at least one spherical shell includes a plurality of connecting holes distributed along the periphery of the at least one spherical shell, and the first ends of the wires are respectively connected to the connecting holes.

9. The minimally invasive surgical instrument according to claim 1, wherein the interior of the intervention device further receive at least one flexible tubular instrument.

10. The minimally invasive surgical instrument according to claim 9, wherein the at least one flexible tubular instruments include an endoscope, an aspiration tube, a perfusion tube, a clip-shaped device, a shearing device, an electrocautery device, or the combination thereof.

11. The minimally invasive surgical instrument according to claim 9, wherein the at least one flexible tubular instruments are extended from the main section to the operation section.

12. The minimally invasive surgical instrument according to claim 1, wherein the at least one wire is extended inside the main section.

13. The minimally invasive surgical instrument according to claim 1, wherein the main section and the operation section of the intervention device are inflexible structures or made of at least one inflexible material.

14. The minimally invasive surgical instrument according to claim 1, further comprising a positioning device configured to fix the top of the intervention device and to position the control device.

15. The minimally invasive surgical instrument according to claim 14, wherein the positioning device includes a housing and a support frame, the support frame is disposed inside the housing, the intervention device is relatively disposed below the housing, the control device is relatively positioned at an upper portion of the housing,
the support frame includes a fixing frame fixed to the housing and a curved frame fixed to the fixing frame, in which
the curved frame holds the sphere to form a ball and socket joint structure such that the sphere is provided with the preset rotational degree of freedom inside the curved frame.

16. The minimally invasive surgical instrument according to claim 14, further comprising a fixing device having a shape of a case, wherein the positioning device is accommodated and positioned in the fixing device.

17. The minimally invasive surgical instrument according to claim 16, further comprising a mistake-proofing device, wherein the mistake-proofing device includes a base portion and at least one latch portions, wherein:
the base portion includes a trunk and a protrusion protruding from the trunk, and the protrusion protrudes toward the sphere,
in an initial state before the sphere rotates, the protrusion is received in a notch of the sphere; and in a steering state that the sphere rotates and the operation section of the intervention device turns, the notch deviates from the protrusion, and the protrusion is pushed and moved by the sphere and the trunk moves accordingly,
wherein the shifted trunk pushes the at least one latch portion, such that the at least one latch portion is engaged with the fixing device so as to fix the positioning device to the fixing device.

18. The minimally invasive surgical instrument according to claim 17, further comprising at least one elastic member, the at least one elastic member is configured to press or pull the at least one latch portion in the initial state, so as to prevent the at least one latch portion from getting stuck with the fixing device in the initial state.

19. The minimally invasive surgical instrument according to claim 1, wherein the entirety of the periphery of the at least one spherical shell is substantially an enclosed circle.

* * * * *